United States Patent [19]
Jodlbauer

[11] Patent Number: 6,090,603
[45] Date of Patent: Jul. 18, 2000

[54] METHOD FOR PRODUCING ENZYMES AND, RESPECTIVELY, ENZYME COMPLEXES

[76] Inventor: Heinz D. Jodlbauer, Drostestrasse 2, D-30161 Hannover, Germany

[21] Appl. No.: 09/191,723

[22] Filed: Nov. 12, 1998

[30] Foreign Application Priority Data

Jan. 28, 1998 [DE] Germany ............... 198 03 070

[51] Int. Cl.$^7$ .................. C12N 9/00; C12N 9/32
[52] U.S. Cl. .................. 435/183; 47/61; 241/8; 241/12; 428/402.2; 435/185; 435/189; 435/198; 435/204
[58] Field of Search ............. 435/183, 185, 435/189, 198, 204; 428/402.2; 241/8, 12; 504/100, 116; 47/61

[56] References Cited

U.S. PATENT DOCUMENTS

| | | |
|---|---|---|
| 5,003,045 | 3/1991 | Hoffman . |
| 5,415,672 | 5/1995 | Fahey et al. . |
| 5,428,147 | 6/1995 | Barker et al. . |
| 5,543,576 | 8/1996 | Van Ooijen et al. . |

FOREIGN PATENT DOCUMENTS

| | | |
|---|---|---|
| 1 442 145 | 10/1968 | Germany . |
| 1 417 568 | 1/1969 | Germany . |
| 20 27 946 | 2/1971 | Germany . |

*Primary Examiner*—Leon B. Lankford, Jr.
*Attorney, Agent, or Firm*—Vidas, Arrett & Steinkraus, P.A.

[57] ABSTRACT

A method of producing enzymes in which plant seeds are subjected to a softening process and a germination process in an aqueous environment and wherein a substance is added to the aqueous environment at least before and during the softening process, the substance selected from the group consisting of liposomes and niosomes and mixtures thereof, the substance containing a germination enhancing factor, the substance relatively easily and rapidly permeating a biomembrane and the germination enhancing factor enhancing the germination process.

25 Claims, No Drawings

METHOD FOR PRODUCING ENZYMES AND, RESPECTIVELY, ENZYME COMPLEXES

BACKGROUND OF THE INVENTION

The present invention relates to a method for producing enzymes and, respectively, enzyme complexes from plant seeds.

So-called technical enzymes in the food and chemical industry are obtained presently by means of mold fungi or bacteria. Quite often it is desirable or necessary to use enzymes produced on a "natural" base.

Such enzymes are known per se. They are produced e.g. by germination of seeds and wheat such as malting of certain wheat types for breweries and distilleries. Barley, wheat and rye malts are produced and used in large amounts. The malting process is a two-step process and consists of the germination phase for producing the so-called green malt and the following kiln-drying process. The result is a more or less aromatized malt product for the beer production having varying contents of enzymes. The kiln-drying process is performed at relatively high temperatures, e.g. up to 105° C. for coloured malts and up to 85° C. for bright malts. As a result the enzymes produced in the germination process are denatured partially or even completely so that their effectiveness gets lost.

Furthermore, it has become known to produce dry cerealia malts which are not kiln-dried such as so-called air or diastase malts. The object of this method is the highest possible enrichment with enzyme complexes at low temperatures.

DE 14 17 568 discloses a method wherein instead of a kiln-drying process treatment of wheat by water vapour or by direct heating thereof with hot vapour is provided. In this method temperatures between 180° C. and 250° C. are used. Inspite of relatively short heating times the temperatures in the germination medium will be increased to 75° C. However, there will be only little or no colouring of the dry malt. Nevertheless, a great part of the enzymes will be denatured also in this temperature range.

DE 20 27 946 discloses a method for treating barley before the malting process. In this method the end of the spelts and parts of the pericarps of the grain remote from the germ is ground off or removed such that a growth substance solution such as gibberellin acid may permeate more thoroughly into the grain so as to accelerate the malting process. While acceleration of the germination process is obtained thereby, the enzyme concentration obtained thereby will nevertheless be in the usual range. The kiln-drying temperatures are also in a conventional range.

DE 14 42 145 discloses a method for treating root germs and cions in a deep temperature range in order to inactivate them so as to obtain an alpha-amylase concentration up to about 65 D.E./g by a gibberellic acid treatment.

All of the above methods suffer from the fact that the obtainable enzyme concentration is relatively small. The use of plant growth substances such as gibberellin can overcome this deficiency not or only partially.

SUMMARY OF THE INVENTION

It is an object of the invention to treat plant seeds so as to obtain significantly increased concentrations of enzymes or enzyme complexes.

The method of the invention is characterized by the following steps:
plant seeds are subjected to a softening process and a germination process in an aqueous environment and
a substance which relatively easily and rapidly permeates a biomembrane and enhances the germination process is added to the aqueous environment at least before and during the softening process.

Liposomes and niosomes are known to permeate through biomembranes relatively easily and rapidly. Liposomes are aqueous compartments which are enclosed by a closed lipid double layer. They are obtained e.g. by suspending suitable lipids in an aqueous solution and treating the resulting mixture by ultra sound. There results a dispersion of closed vesicles of substantially the same size. Alternatively, such vesicles may be obtained by rapidly mixing a lipid solution with water. When the lipid is injected into the aqueous solution by a thin syringe, round vesicles of a diameter of e.g. 50 nm result. However, also chemically synthetic liposome formers are known. They are so-called niosomes.

In connection with the invention it was found that the germ of a plant seed, in particular the scutellum together with the growing suction epethelium, may be used as a chemical reactor by the described substance to provide for an activation effect. The plant seeds are subjected—as in a malting process—to a conventional softening process and germination process in an aqueous environment. However, the liposomes or niosomes permeating through the biomembrane are being added to the aqueous environment. On the one hand, this results in an increased activation of the seed inherent gibberellins. On the other hand, this results in use of the seed inherent distribution net, i.e. enhanced conveyance of gibberellins to the aleuron layer and return conveyance of reserve substances from the flour body to the germ. Apparently, activation of the enlarged "receiving surface of the suction epithelium" has a positive effect. As a result of the activation of the growth substances and conveyance to the aleuron layer with the aim to enhance formation of enzymes and, respectively, enzyme complexes, enrichment with certain enzymes such as alpha-amylase, beta-amylase, beta-glucanase, pentosonase, oxidase, lipoxigenase, phospholipase, phospatase, lipase and special proteases is being initiated. At the same time the described process may be accompanied by suppression of certain enzymes and enzyme complexes. Altogether the ratio of the length of the germ to the length of the flour body in connection with the resolution degree (stark resolution) plays a significant role.

The described substances form a carrier which enhances conveyance in the interior of the plant seed after it has entered thereto. It was found that enzyme concentration in the germinated material can be increased thereby to an extraordinary level not known so far.

In an embodiment of the invention the liposomes are made from lecithin or a lecithin fraction. For example, a lecithin which primarily contains phosphatidylcholin (PC) can be used. As an alternative a lecithin fraction of phosphatidylethanolamin and phosphatidylinositol (PE and PI) may be used. When niosomes are used, an embodiment of the invention provides that alkylpolyglycerinether together with cholesterin and diacetylphosphate or a glycero-lactyl-palmitate may be used as niosome formers.

The vesicles of the used liposomes and niosomes are of a size in the order of 10 to 3000 nm, preferably 50 to 200 nm.

In a further embodiment of the invention the liposomes or niosomes are loaded by a loading substance enhancing the formation of enzymes. The loading of antiliposomes or—niosomes with a biocatalyst is known per se and is obtained by methods known in the industry. The type of biocatalyst as used is of decisive importance. Depending on whether the biocatalysts are lipophil, hydrophobe or hydrophil substances the loading occurs in the hull or in the interior of the liposome. Biocatalysts of lipophil or hydrophobe character such as for example indoly-3-acetic acid (IAA) or gibberellic acid (GA) are enclosed in the hull (also known as bilayer membrane), and hydrophil substances such as ions or salt solutions are enclosed within the interior and may readily reach the provided centers.

According to a further modification of the invention the method of the invention may use as loading substances a number of substances such as monovalent, bivalent or multivalent ions such as chlorides, phosphates, ammonium, calium, calcium, magnesium, copper, manganese and/or iron, organic acids such as ascorbic acid, acetic acid, amino acids. The amino acids may be for example tryptophan, lactic acid, orotic acid, guanine, guanidine, adenosine-5-triphosphate dinatrium (ATP) as well as growth substances (also known as growth regulators) such as gibberellins (GA) and abscisic acid (ABA) alone or in combination may be used. In a liposome solution the average diameter of the liposomes is preferably in the order of 100 nm. It is possible to use not only monolayer and bilayer structures but also mixed structures (multilayer structures) may be used. When there is loading with a biocatalyst, the liposome serves as a conveying medium for conveyance to the active germ centers and, respectively, active enzyme centers in the biological material. Depending on the polarity of the loading substance encapsulation occurs in the bilayer area, i.e. in the lipophil portion or in the hydrophil portion of the vesicles, i.e. in the interior of the sphere. A specialty is the encapsulation of technical enzymes such as cellulase or hemicellulase in order to partially remove e.g. the outer layers of the seed grain. This allows the biocatalyst more quickly to enter into the interior of the seedling.

In an embodiment of the invention the treatment phase, i.e. subjecting the seedlings to water and the activating substance takes from 1 to 12 hours. The softening phase takes preferably from 1 to 6 hours. The germination phase takes from 2 to 10 days, preferably 3 to 4 days. The temperature prevailing during the germination phase preferably will be controlled and will be kept to relatively low values such as between 10 and 25° C., preferably 14 to 15° C. To this end continuous cooling, preferably by air, is usually provided.

After a predetermined duration the germination phase is interrupted. To this end the invention provides that the interruption is obtained by shock freezing. To this end temperatures from −10° C. to−40° C., preferably about−16° C., are used. After termination of the germination phase preferably drying of the germination material is provided. To this end freeze-drying known per se may be used. In an embodiment of the invention the material will be set to have a water content of 3 to 10%, preferably 6%.

To obtain the enzymes and, respectively, the enzyme complexes from the germination material, preferably the latter will be ground. The ground material may then be separated into a fraction rich in enzymes and proteins and a fraction poor in proteins and enzymes. Preferably this is obtained by winnowing. Such methods are known per se.

EXAMPLES OF THE INVENTION

A liposome solution may be obtained in accordance with the following recipe:

| | |
|---|---|
| phosphorlipid fraction (with a phosphatidylcholin content of 40%) | 5,000 |
| water | 45,000 |
| | 50,000 |

Before use the liposome solution will be diluted as follows:

| | kg |
|---|---|
| liposome solution | 50,000 |
| water | 100,000 |
| | 150,000 |

Further dilution may be obtained according to the following example:

| | |
|---|---|
| 1st dilution solution | 150,000 |
| water | 7500,000 |
| | 7650,000 |

In this example the final liposome solution contains 0.065% liposome.

The above figures are weight percentages. This is true also for the figures of the following examples.

The described liposome solution may be used for example for treatment of wheat or soja beans.

The following is an example for treatment of wheat for a duration of 1 to 12 hours:

| | kg |
|---|---|
| wheat | 3,000 |
| final liposome solution | 2,250 |
| total amount | 5,250 |
| ./. not absorbed liposome solution | 1,480 |
| total used liposome solution | 2,250 |
| liposome solution absorbed by wheat | 1,770 |

Softening Phase:
  Treatment duration between 1 to 6 hours

| | |
|---|---|
| wheat + liposome | 4,770 |
| depending on the softening conditions up to | 1,000 |
| 1,000 kg water for remoistening in the germination phase | |
| | 5,770 |

Germination Phase:
  Duration between 2 to 10 days, preferably 4 days depending on the desired enzyme profile. Temperature ranges between 10° C. to 25° C., preferably 14° C. to 15° C.
Germination conditions: conventional germination boxes, as an alternative drum malting systems may be used.

Cooling Phase:

Cooling is performed during all three phases, with the desired pilot temperature for obtaining the desired enzyme profile is controlled by means of the amount of cooling air.

Freezing Phase:

When the desired enzyme profiles will have been obtained in the germination material, the freezing phase is inititiated to stop the germination phase at a temperature in the range from −10° C. to −40° C., preferably at−16° C. by shock freezing in order to prevent any further change of the produced enzyme profile.

Drying Phase:

The freezing phase is followed by the drying phase for producing stable dry products. In order to avoid enzyme losses conventional kiln-drying should not be used; rather, one of the most gentle drying methods such as freeze drying is being used in order to retain the produced enzymes in the dried material to the largest possible extent. The freeze-dried product will be set to have a water content of between 3 and 10%, preferably 6%.

Furthermore, it is possible to use the undried deep frozen germination material, e.g. directly in large bakeries and in the food industry. For stabilizing and preservatizing purposes the germination material may be inoculated with lacto bacteria cultures in order to reduce the pH value. The bacteria culture is introduced into the liposome solution preferably during the production phase. Adding an acid, preferably in the initial germination phase, enhances substantially the activity of the lactic acid bacteria.

Enzyme profiles play an important role in connection with present baking substances, in particular for the stopping of fermentation in bakeries, and supplement the function of chemically synthetic emulsifiers. To date only chemically synthetic enzymes, so-called technical enzymes, have been used for this purpose. The method of the present invention allows to produce the desired enzymes and enzyme profiles on a plant base, their use is advantageous not only in the food industry but also in the chemical industry.

Due to "induction" of the germination system, for example in wheat or leguminoses, specific enzyme profiles are produced, with all required enzymes being available in plant seeds. In the following four examples of the present invention for the production of enzymes will be described and compared to otherwise produced enzyme concentrations.

TABLE 1

WHEAT
Enzyme profile

|  | Alpha-amylase U/g TrS | Lipoxy-genase U/g Trs pH 9.0 | Phos-phorlipase C mmol/min/g |
|---|---|---|---|
| wheat green malt 6 days germination without heating | 440 | 25870 | 18.5 |
| wheat kiln-dried malt 6 days germination max. kiln temperature ca 80° C. | 63 | 929 | 7.9 |
| wheat germination after liposome treatment, there-after freeze dried + germs | 1223 | 60021 | 34.3 |

TABLE 2

SOJA BEANS
Enzyme profile

|  | Alpha-amylase U/g TrS | Lipoxygenase U/g TrS pH 9.0 |
|---|---|---|
| 6 days germination without heating | 5.7 | 1476651 |
| 6 days germination with liposome treatment, freeze-dried + germs | 4.8 | 4330080 |

TABLE 3

ALPHA-AMYLASE contents U/g TrS

|  | barley | rye | beans |
|---|---|---|---|
| no germination | 0.8 | 4.1 | 2.3 |
| 3 days germination with liposoine treatment, freeze-dried | 3530 | 2080 | 5.0 |

TABLE 4

FIELD BEANS

|  | Alpha-Amylase U/g TrS | Lipoxygenase U/g TrS pH 6.0 | Lipase U/g TrS |
|---|---|---|---|
| 8 days germination with liposome treatment, 0.05 molar CaCl-ions, freeze-dried | 2.51 | 4070 | 32.90 |
| 8 days germination with liposome treatment, 0.05 molar MgCl-ions, freeze-dried | 0.96 | 6330 | 58.50 |

The above tables show the enrichment with specific enzyme profiles according to the invention. As may be seen the invention allows to obtain enzyme concentrations in plant materials not possible so far.

The following is an example of a large-scale test:

Tested mass: 2000 kg wheat—cleaned in a conventional manner

Duration of test: 6 days

Test system (pilot system):

Germination boxes (saladin boxes), capacity:

36 t with zone regulation, conventional cooling (refrigerant evaporator); aeration is performed by means of fans, minimal loading capacity is about 1 t. The turning system comprises turning vehicles and turning helices; loading amounts up to 5 t were turned manually.

Liposome treatment (according to the above description) +softening: 12 hours. The treatment resulted in a temperature increase of 5.5° C. (soaking temperature 9.7° C., end temperature 15.2° C.).

Temperature measurement at the beginning of the germination test

Temperature at the appliance shed: T° above the hurdle: 16.5° C.

below the hurdle: 15.0° C.

return air: 100% to 95% fresh air: 0%

Temperature:

| germination days | temperature ° C. directly measured in the material | | |
|---|---|---|---|
| | morning | midday | evening |
| 1st day | 15.3 | 14.5 | 17.0 |
| 2nd day | 14.7 | 13.4 | 13.5 |
| 3rd day | 13.9 | 13.7 | 14.2 |

Water content in the germination material after the 3rd day: 39,1%

Temperature at the appliance shed after the 3rd day: T° above the hurdle: 16,0° C.

below the hurdle: 14.5° C.

return air: 94% fresh air: 22%

| 4th day | 13.5 | 13.6 | 14.1 |
|---|---|---|---|
| 5th day | 13.9 | 14.7 | 14.9 |

Temperature at the appliance shed after the 5th day: T° above the hurdle: 16,9° C.

below the hurdle: 16,5° C.

return air: 95% fresh air: 22%

| 6th day end | 14.7 | 15.2 | 15.1 |
|---|---|---|---|

The continuous wetting of the germination material was obtained manually on the principle of watering cans under consideration of the practical malster experience.

The germination material obtained thereby was at once deep frozen by conventional methods and freeze-dried.

The germination test is being controlled via the temperature in the germination material. Of particular importance is the abrupt change of the temperature after the liposome treatment.

The effectiveness of the liposome treatment in connection with the 6-days-germination is determined by determining the enzyme profile by means of a chemical analysis and a standard baking test (RMT-baking test).

The large-scale test resulted in the following values of the enzyme profile:

Chemical Analysis:

| | Alpha-amylase U/g TrS | Lipoxygenase U/g TrS pH 6.0/9.0 | phosphorus lipase mmol/min/g |
|---|---|---|---|
| 6 days germination of wheat after liposome treatment, frozen and freeze-dried + germs | 1039 | 1498/9435 | 30.2 |

Baking test modified according to RMT standard baking test

| Recipe: | 1000 g flour type 550 |
|---|---|
| | 550 g water |
| | 50 g yeast |
| | 20 g salt |
| | 10 g sugar |
| | 10 g biskin |

Dough temperature: 25–26° C.

Result:

| | 0 test only flour | with enzyme preparation incl. germs added mass: 5 g + 995 g flour 0.5% |
|---|---|---|
| Baking volume (ml) | normal fermentation: 3250 | normal fermentation: 3790 |
| | excessive fermentation: 3030 | excessive fermentation: 3670 |

Enzyme profiles produced in accordance with the invention can be used in varying concentrations with conventional baking recipes which have been produced up to now on the base of chemically synthetic emulsifiers. Preferably they are used with baking recipes which include lecithins and, respectively, lecithin fractions as emulsifiers. The technical enzymes used in connection with these conventional baking recipes can be completely substituted by the enzyme profiles in the form of mixed preparations of various plant materials in accordance with the present invention. The following example is such a baking recipe:

Type designation AKH 156

| | % |
|---|---|
| guar core flour | 20.000 |
| dextrose | 20.000 |
| saccharose | 10.000 |
| ascorbic acid | 0.250 |
| IM10 | 15.000 |
| UM20 | 3.750 |
| LC 2000 (30%) | 30.000 |
| ES 1000 | 1.000 |
| | 100.000 |

IM 10: wheat, 6 days germination after liposome treatment, freeze-dried, ground and partially winnowed, resulting in an enzyme profile as already described.

UM 20 winter barley, 3 days germination after liposome treatment, freeze-dried and ground, with enzyme profile as already described.

ES 1000: soja beans, 6 days germination after liposome treatment, freeze-dried and ground, partially winnowed, with enzyme profile as already described, dilution 1:10000

LC 2000: 30% lecithin mixture on the basis of wheat flour; the lecithin is a lecithin fraction according to EP 0 245 723 B1.

A product was obtained by baking in accordance with the above baking recipe and compared to a product sold in the German market under the tradename "Goldmalz". The following baking protocol sets forth the baking results. From this follows that an enzyme profile produced by the method of the invention has baking qualities equivalent to conventional enzymes, preferably in the deep cooling area with fermentation delay and fermentation stopping.

Baking Protocol:

| Date: April 21, 1997 Rapid-Mix-Test | | | | |
|---|---|---|---|---|
| Designation of specimen | AHK-156 | | Goldmalz | |
| Amount of flour (Roland 550) | 1000 | | 1000 | |
| Liquid (ml) | 590 | | 590 | |
| Yeast (g) | 50 | | 50 | |
| Salt (g) | 15 | | 15 | |
| Baking substance (g) | 25 | | 25 | |
| Fat P 1 (g) | 10 | | 10 | |
| Peanut fat (g) | — | | | |
| Sugar (g) | — | | | |
| Temperature of dough (° C.) | 25.8 | | 25.7 | |
| Dough weight | 1693 | | 1683 | |
| Dough quality | | | | |
| Surface | normal | | normal | |
| Resilience | normal | | smooth | |
| Fermentation time (min) | 25 | 30 | 25 | 30 |
| Dough weight (g) (from 15 increased to 30) | 1688 | 1692 | 1690 | 1678 |
| Weight of baked goods (from 15 increased to 30) | 1284 | 1290 | 1278 | 1284 |
| Baking loss (%) | 23.9 | 23.2 | 24.4 | 23.4 |
| Volume of baked goods crusted (cm³), at least 15 | 6800 | — | — | — |
| Volume of baked goods pressed (cm³) | 6800 | 6780 | 6550 | 6600 |
| Baked goods crusted | | | | |
| Grade | good | still good | still good | poor |
| Type | — | narrow | narrow | all not crusted |
| Browning | normal | normal | normal | normal |
| Crispness | | | | |
| Grade | good | good | good | still good |
| Type | — | — | — | somewhat splintery |
| Uniformity of pores | rather uniform | uniform | uniform | rather uniform |
| Crumb resilience | still good | still good | still good | still good |
| Taste | faultless | faultless | faultless | faultless |
| Buns crusted/not crusted | 15/0 | 8/7 | 8/7 | 0/15 |
| Remarks | | | some not suited for treatment by machine (6 of 30 dough goods) | |

What is claimed is:

1. A method of producing enzymes comprising the following steps:

subjecting plant seeds to a softening process and a germination process in an aqueous environment and adding a substance to the aqueous environment at least before and during the softening process, the substance selected from the group consisting of liposomes and niosomes and mixtures thereof, the substance containing a germination enhancing factor, the substance relatively easily and rapidly permeating a biomembrane and the germination enhancing factor enhancing the germination process.

2. A method according to claim 1 wherein the liposomes are made from lecithin or a lecithin fraction.

3. A method according to claim 2 wherein the lecithin contains primarily phosphatidylcholin.

4. A method according to claim 2 wherein a lecithin fraction containing phosphatidylethanolamin and phosphatidylinositol is used.

5. A method according to claim 1 wherein an alkylpolyglycerinether together with cholesterin and diacetylphosphate or a glycero-lactyl-palmitate is used for production of the niosomes.

6. A method according to claim 1 wherein the substance is comprised of vesicles, the vesicles ranging in size from 10 to 30 nm, preferably 50 to 200 nm.

7. A method according to claim 1 wherein monovalent, bivalent or multivalent ions such as chloride, phosphate, ammonium, calium, calcium, magnesium, copper, manganese and/or iron are used as the germination enhancing factors loading substance.

8. A method according to claim 1 wherein organic acids such as ascorbic acid, acetic acid and/or amino acids are used as the germination enhancing factors.

9. A method according to claim 8 wherein the amino acids are tryptophan, lactic acid, orotic acid, guanine, guanidine or adenosin-5-tri-phosphate dinatrium.

10. A method according to claim 7 wherein growth substances are used as the germination enhancing factor.

11. A method according to claim 10 wherein gibberellins, abscisic acid or a combination thereof are used as growth substances.

12. A method according to claim 1 wherein the phase of treatment with said substance is from 1 to 12 hours.

13. A method according to claim 1 wherein the softening phase is from 1 to 6 hours.

14. A method according to claim 1 wherein the germination phase is from 2 to 10 days, preferably 3 to 4 days.

15. A method according to claim 1 characterized by providing, during the germination phase, a temperature of 10 to 25° C., preferably 14 to 15° C.

16. A method according to claim 1 characterized by cooling during the individual phases.

17. A method according to claim 16 wherein air is used for cooling.

18. A method according to claim 1 wherein the germination phase is stopped after expiry of a predetermined duration of the germination phase.

19. A method according to claim 18 wherein the stoppage is obtained by shock freezing.

20. A method according to claim 19 wherein said shock freezing is performed at a temperature of −10° C. to −40° C., preferably at −16° C.

21. A method according to claim 1 characterized by initiating a drying phase after termination of the germination phase.

22. A method according to claim 21 characterized by a freeze-drying phase.

23. A method according to claim 21 characterized by setting a water content of 3 to 10%, preferably of 6%.

24. A method according to claim 1 wherein the germination substance is ground after the drying phase.

25. A method according to claim 24 wherein the ground substance is subdivided, preferably by winnowing, into two fractions, namely a fraction rich in proteins and enzymes and a fraction poor in proteins and enzymes.

* * * * *